United States Patent [19]

Bolz et al.

[11] 4,025,310

[45] May 24, 1977

[54] METHOD FOR READING A WET FLUORESCENT SURFACE

[75] Inventors: Gunner Bolz, Santa Clara; Fred H. Deindoerfer, Northridge; Charles R. Gifford, Santa Clara; Naomi Kameda, Foster City, all of Calif.

[73] Assignee: International Diagnostic Technology, Inc., Santa Clara, Calif.

[22] Filed: May 28, 1976

[21] Appl. No.: 690,975

[52] U.S. Cl. .............................. 23/230 B; 250/302; 424/12
[51] Int. Cl.² ................. G01N 21/22; G01N 33/16
[58] Field of Search ................. 23/230 B; 250/302; 424/7, 12

[56] References Cited

UNITED STATES PATENTS

| | | | |
|---|---|---|---|
| 2,770,572 | 11/1956 | Eldon | 23/230 B |
| 3,826,613 | 7/1974 | Parikh et al. | 23/230 B |
| 3,916,205 | 10/1975 | Kleinerman | 250/461 B |

*Primary Examiner*—Robert M. Reese
*Attorney, Agent, or Firm*—Flehr, Hohbach, Test, Albritton & Herbert

[57] ABSTRACT

An improved method for the fluorometric measurement of a fluorescent label on a solid support surface in which the surface is read while coated with a continuous aqueous layer. For reading in a horizontal position, the surface is coated by immersion into a contained aqueous solution, and removed and read prior to evaporation to discontinuity. For reading in a vertical position, a layer of humectant is deposited on the surface to retain the water content.

13 Claims, No Drawings

METHOD FOR READING A WET FLUORESCENT SURFACE

CROSS-REFERENCE TO RELATED APPLICATIONS

Reference is made to co-pending Deindoerfer et al application Ser. No. 627,941, filed Nov. 3, 1975, entitled "Diagnostic Reagent Holder and Method" and to application Ser. No. 553,582, filed Feb. 27, 1975, entitled "Fluorometric System, Method and Test Article," in the name of Richard A. Harte, now U.S. Pat. No. 3,992,631.

BACKGROUND OF THE INVENTION

In a solid-phase support system disclosed in patent application Ser. No. 627,941, filed Nov. 3, 1975, a sample is sorbed onto a reaction support surface (e.g., disc) carried by a diagnostic reagent holder. Antigen or antibody in the sample is labelled as with a fluorogen for quantitative reading of the surface by a fluorometer through a window in a viewing housing which precisely positions the surface. The disc and holder are illustrated in a vertical position.

SUMMARY OF THE INVENTION AND OBJECTS

In accordance with the present invention, an improved method is provided for the fluorometric measurement of a fluorescent label on a solid support surface. The surface is read fluorometrically while coated with a continuous aqueous layer but without being immersed in a defined liquid volume. It has been found that such reading minimizes drift of the intensity of fluorescence read by the fluorometer over a given time interval. When the fluorescent label is coated onto the surface by immersion in and removal from a contained aqueous solution of the label, the reading is performed prior to evaporation to discontinuity of the aqueous layer which adheres to the surface. The reading is preferably performed with the surface in a horizontal position so that the liquid can spread uniformly. Alternatively, the surface can be read in a vertical position by coating it with a layer of humectant which retains the water content of the same.

It is an object of the invention to provide an improved method for the fluorometric measurement of a fluorescent label on a solid support surface which provides a constant fluorometric reading during the time required for reading.

Further objects and features of this invention will be apparent from the following description of the preferred embodiment of the same.

DETAILED DESCRIPTION OF THE PREFERRED EMBODIMENTS

The present invention relates generally to a method for the fluorometric measurement of a fluorescent label on a solid support surface. This system is particularly useful in the quantitation of a fluorescently labelled antigen or antibody which is coated on a reaction support surface such as a disc carried by a holder as described in detail in co-pending application Ser. No. 627,941, filed Nov. 3, 1975, incorporated herein by reference. The disc may be formed of a suitable material such as polyacrylic, polyamide, cellulosic or other polymeric materials. The holder includes a convenient handle at one end and a surface for mounting the disc at the other end as by a suitable adhesive. The handle includes an elongate shaft of suitable length for gripping the holder for stirring or the like. A protective liquid retaining rim is disposed around the periphery of said surface which serves a function set forth hereinafter.

Various techniques for measuring such fluorescently labelled substances are described in co-pending application Ser. No. 553,582, filed Feb. 27, 1975, entitled "Fluorometric System, Method and Test Article." Such techniques are incorporated at this point by reference. In one such technique, known by immunologists as the "sandwich technique", an antibody to the specific antigen to be detected is first coated onto the disc. In a typical instance, the test is for "Australian Antigen" in the blood which is regarded as prima facie evidence of hepatitis infection. The AntiAustralian antigen-antibody is coated on the disc. Then the disc is immersed by the handle in a volume of liquid sample constituting the serum of the subject suspected of carrying the antigen. If the antigen is present, it binds immunologically to the antibody on the disc. After rinsing with wash solution to remove unbound material, more antibody with a fluorescent label is added which binds to the antigen. Then a final rinse removes unbound labelled antibody. In a fluorometric system, the fluorescence emitted from the coating is detected by a fluorometer.

It has been found that when the support surface is read in a vertical position, there is a significant drift with time in the level of detected fluorescence. It is believed that this drift is due to an unexpected variance of the fluorescent signal as a function of the continuity of the water content remaining on the surface.

Coating of the fluorescent label typically involves one or more immunological reactions occuring on the surface while immersed in a contained aqueous solution. When the surface is removed from such contained solution and positioned in a vertical direction for reading, the water content of the surface rapidly drains producing discontinuity of the aqueous layer which adheres to the surface. As mentioned above, it is believed that such discontinuity is a cause of drift of the signal. Thus, the aqueous layer serves as a buffer to stabilize the signal.

The aqueous layer also enhances the optical properties of the surface for transmitting a maximum fluorescent signal. If the surface is permitted to drain completely, the fluorescence signal is significantly lowered, a disadvantage when only a relatively small quantity of fluorescently labelled substance deposits onto the surface. Another reason to avoid complete drying of the surface is that it adds another step which slows the overall procedure, an important factor in any analytical technique. Furthermore, the surface is hygroscopic to some extent, so that it would be difficult to dry uniformly and there could be variances in moisture content from one surface to another. This could lead to an undesirable variation in analytical precision.

A preferable technique for depositing a continuous aqueous layer onto the surface is by immersion in and removal from a contained aqueous solution. Then, the fluorometric reading is performed prior to evaporation to discontinuity of the aqueous layer which adheres to the surface. At ambient temperatures, such readings suitably are taken within about one to three minutes from removal from the liquid. When the fluorescent label is attached to protein such as antigen or antibody as for use in immunological quantitation, the last step of the procedure generally constitutes immersing the surface into a contained aqueous solution for washing. In this instance, by reading of the surface prior to evaporation to discontinuity of the aqueous layer adhered to the surface during the analytical technique, the time for permitting the surface to dry and thereafter for wetting the same by immersion in a separate aqueous solution may be avoided.

It has been found that reading of the surface in an essentially horizontal position prevents rapid drainage of the aqueous solution and so permits a longer period of time for reading of the surface after removal from solution. Thus, a steady reading is obtained so long as the surface is read prior to evaporation to discontinuity of the aqueous layer. By essentially horizontal, minor variations from the horizontal such as about 10° may be tolerated without undue drainage.

Referring again to co-pending application Ser. No. 627,941, it is preferable that the disc by positioned into the viewing housing in a horizontal position rather than the illustrated vertical position. This can be accomplished by turning the viewing housing onto its side.

The preferred horizontal position is with the wet support surface facing upwardly. However, even facing the horizontal surface downwardly retains liquid better than disposing the surface in a vertical direction.

If, for some reason it is not practical to read the surface in a horizontal position, it may be read in a relatively vertical position if done extremely rapidly prior to any drainage. This would be a difficult procedure to reproduce precisely. A longer time interval is made possible by addition of a humectant to the aqueous solution layered on the surface. This retains the water content on the surface by inhibiting evaporation and providing sufficient viscosity to minimize drainage. A preferable viscous humectant is glycerin. However, other viscous humectants such as polyvinyl alcohol, hydroxyethyl cellulose, and sorbitol may also be employed for this purpose. There are certain disadvantages to the use of a humectant to prevent discontinuity of the aqueous liquid. An additional step and reagent is required. Also, it has been found that it is preferable to store the surface in a horizontal position for a sufficient time (e.g., 5 to 10 minutes) to equilibrate the humectant on the surface. Otherwise, the signal tends to drift even in the presence of the humectant.

One technique for minimizing liquid drainage is to provide a liquid retaining wall around the periphery of the wet solid support surface. One embodiment of such a wall is the rim of the holder of the aforementioned application Ser. No. 627,941.

The continuous aqueous layer maintained on the solid support surface of the present invention is in a relatively thin film and is free of any liquid volume contained independently of the surface during the reading. The only external restraint on the liquid is imposed by the peripheral wall surrounding the surface described in the preceding paragraph. This excludes reading the support surface in a defined volume of liquid such as in a test tube filled with liquid. The presence of a defined liquid volume of the latter type prevents precise viewing as described in the aforementioned application Ser. No. 627,941. Also, viewing accuracy is impeded by reading through the test tube wall and larger liquid volumes. Another disadvantage is that a different tube of liquid should be employed for each reagent holder to prevent contamination from carryover.

The fluorescent signal from the solid support surface is received by the optical fluorescence collection end of a fluorometer. The surface is exposed to the ambient atmosphere. Thus the fluorometer collection end is spaced apart from the thin aqueous layer or film on the support surface. This arrangement avoids problems of contamination of the fluorometer. It also facilitates rapid reading immediately after the final rinse step of a diagnostic procedure.

Reading the surface at a temperature which is within approximately 5° C of the aqueous solution in which it is last immersed also reduced signal drift. It has been found that the signal intensity is relatively sensitive to larger temperature differentials. Typically, the aqueous solution is maintained at ambient temperatures. Thus, it is preferable that the reading of the fluorescent signal also take place at ambient temperatures. A heat sink may be employed in the fluorometer housing to prevent temperature variations.

A further disclosure of the nature of the present invention is provided by the following specific examples of the practice of the invention. It should be understood that the data disclosed serve only as examples and are not intended to limit the scope of the invention.

EXAMPLE 1

The following example illustrates stabilization of the signal from the surface of a reagent holder of the type described herein read by a fluorometer in a vertical position by the addition of a humectant, glycerol. The holder is immersed into the final wash solution (phosphate buffered saline solution) and then allowed to dry in ambient conditions. In run A, no humectant is present. In run B, 40% glycerol is added to the final rinse solution.

The surface of both runs comprised an immune complex of human immunoglobulin G and fluorescein isothiocyanate labelled goat anti-human immunoglobulin G antibody on a polyacrylic surface.

| Fluorescent Signal in Relative Units | | |
|---|---|---|
| | Wash Solution | |
| Time After Removal, minutes | Run A (Without Humectant) | Run B (With Humectant) |
| 0 | 1.000 | 1.000 |
| 5 | 0.891 | 1.101 |
| 10 | 0.870 | 1.116 |
| 15 | 0.837 | 1.125 |
| 20 | 0.826 | 1.136 |
| 50 | 0.728 | 1.104 |

In Run A, the surface without glycerol drops off in signal almost twenty percent over the 45 minutes following a ten percent drop in the first five minutes. In Run B, the surface with glycerol varies less than four percent in the 45 minutes following the initial 5 minutes.

EXAMPLE 2

The following example illustrates that the vertical instability can be overcome by reading the same type of surface as described in Example 1 horizontally after its removal from a phosphate buffered saline wash solution and immediately placed in the fluorometer.

| Time, Seconds | Vertical Reading Fluorescent Signal, Relative Units | | |
| --- | --- | --- | --- |
| | Run A | Run B | Run C |
| 0 | 1.000 | 1.000 | 1.000 |
| 20 | 1.000 | 1.007 | 1.015 |
| 40 | 1.008 | 1.017 | 1.027 |
| 60 | 1.020 | 1.024 | 1.036 |
| 80 | 1.033 | 1.033 | 1.045 |
| 100 | 1.048 | 1.043 | 1.049 |

The drift in signal when the surface read is in a vertical position averages approximately 3% per minute. Such drift can cause large errors when many samples are being read.

| Time, Minutes | Horizontal Reading Fluorescent Signal, Relative Units | | |
| --- | --- | --- | --- |
| | Run A | Run B | Run C |
| 0 | 1.000 | 1.000 | 1.000 |
| 1 | 1.002 | 1.004 | 1.007 |
| 2 | 1.012 | 1.004 | 1.007 |
| 3 | 1.012 | 0.996 | 0.996 |
| 4 | 1.010 | 0.989 | 0.991 |
| 5 | 1.008 | 0.985 | 0.986 |

When read horizontally, similar surfaces exhibited 1.5% or less drift in five minutes, a condition much more stable than reading in a vertical position.

What is claimed is:

1. In an improved method for the quantitative measurement of the signal from a fluorescent label on a solid support surface received by the optical fluorescence collection end of a fluorometer, the improvement comprising fluorometrically reading the signal while the surface is coated with a continuous aqueous layer, said surface being exposed to the ambient atmosphere and being free of a liquid volume contained independently of the surface during said reading, said fluorometer collection end being spaced apart from said aqueous layer.

2. The method of claim 1 in which the last step of depositing said fluorescent label onto said surface includes immersion in and removal from a contained aqueous solution, said reading being performed prior to evaporation to discontinuity of the aqueous layer which adheres to said surface.

3. The method of claim 1 in which said fluorescent label comprises a fluorescently labelled protein to be quantitated.

4. The method of claim 1 in which the temperature of said aqueous layer is within about 5° C of the temperature of said surface during reading.

5. The method of claim 1 in which said surface is immersed in and removed from a contained aqueous solution and said reading is performed prior to evaporation to discontinuity of the aqueous layer which adheres to said surface.

6. The method of claim 5 in which said surface is read within about 5 minutes from removal from said contained liquid.

7. The method of claim 1 in which said surface is in an essentially horizontal position facing upwardly during reading.

8. The method of claim 7 in which said surface is attached to a handle, and a liquid retaining rim is disposed around the periphery of said surface to minimize liquid drainage.

9. The method of claim 7 in which said support surface is attached to a handle and is precisely positioned in a viewing housing during reading.

10. The method of claim 1 in which a layer of humectant is deposited on said surface to retain its water content.

11. The method of claim 10 in which said humectant layered surface is equilibrated in an essentially horizontal position prior to reading.

12. The method of claim 10 in which said humectant contains a material selected from the group consisting of glycerin, polyvinyl alcohol, hydroxyethyl cellulose, sorbitol and mixtures thereof.

13. The method of claim 10 in which said humectant contains glycerin.

* * * * *